(12) United States Patent
Steck et al.

(10) Patent No.: US 6,364,860 B1
(45) Date of Patent: Apr. 2, 2002

(54) RESETTABLE DISPLAY OF A DEVICE FOR METERED ADMINISTRATION OF A FLUID DRUG

(75) Inventors: Jürg Steck, Kirchberg; Thomas Gurtner, Koppigen, both of (CH)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 09/092,529

(22) Filed: Jun. 5, 1998

(30) Foreign Application Priority Data

Jun. 5, 1997 (DE) ......................... 197 23 647

(51) Int. Cl.⁷ .............................................. A61M 5/00
(52) U.S. Cl. ...................... 604/246; 604/207; 604/211; 604/214
(58) Field of Search ............................ 614/246, 32, 68, 614/71, 207, 208, 211; 222/43, 46, 336, 309; 604/186–88, 209, 210, 214, 232, 246

(56) References Cited

U.S. PATENT DOCUMENTS

| 4,865,591 A | | 9/1989 | Sams | 604/186 |
|---|---|---|---|---|
| 4,950,246 A | | 8/1990 | Muller | 604/154 |
| 5,092,842 A | * | 3/1992 | Bechtold et al. | 604/135 |
| 5,279,586 A | * | 1/1994 | Balkwill | 604/207 |
| 5,295,976 A | | 3/1994 | Harris | 604/211 |
| 5,582,598 A | | 12/1996 | Chanoch | 604/208 |
| 5,584,815 A | * | 12/1996 | Pawelka et al. | 604/191 |
| 5,593,390 A | | 1/1997 | Castellano | 604/187 |
| 5,674,204 A | | 10/1997 | Chanoch | 604/211 |
| 5,725,508 A | | 3/1998 | Chanoch | 604/207 |
| 5,728,074 A | | 3/1998 | Castellano | 604/207 |
| 5,743,889 A | | 4/1998 | Sams | 604/211 |
| 5,807,346 A | | 9/1998 | Frezza | 604/208 |
| 6,059,755 A | | 5/2000 | Michel | 604/207 |
| 6,086,567 A | * | 7/2000 | Kirchhofer et al. | 604/211 |
| 6,090,080 A | | 7/2000 | Jost | 604/207 |
| 6,096,010 A | * | 8/2000 | Walters et al. | 604/207 |

FOREIGN PATENT DOCUMENTS

| DE | 4013769 | 10/1991 |
|---|---|---|
| DE | 4112259 | 10/1992 |
| DE | 4223958 | 1/1993 |
| EP | 0058536 | 8/1982 |
| EP | 0327910 | 8/1989 |
| EP | 0496141 | 7/1992 |
| EP | 0554996 | 1/1993 |
| EP | 0581925 | 2/1993 |
| EP | 0554995 | 8/1993 |
| EP | 0730876 | 9/1996 |
| WO | 9316740 | 9/1993 |
| WO | WO9415120 | 7/1994 |
| WO | WO9415660 | 7/1994 |
| WO | WO9607443 | 3/1996 |
| WO | WO9730742 | 8/1997 |
| WO | 98/01172 | * 1/1998 |

* cited by examiner

*Primary Examiner*—Angela D. Sykes
*Assistant Examiner*—Patricia Bianco
(74) *Attorney, Agent, or Firm*—Dorsey & Whitney LLP

(57) ABSTRACT

A resettable display of a device for metered administration of a fluid drug, comprising a housing, a fluid container containing the fluid and provided in or on said housing, an actuating device shiftably mounted by a length in or on said housing, which, upon actuation, shifts a piston in the fluid container in order to displace from the fluid container a fluid dose adjusted by the actuating device, a display provided in or on said housing displaying a measure for the adjusted fluid dose, and a resetting means shifted with the actuating device and thus resetting the display. The display comprises a minimum of one counter ring rotated from a zero position when adjusting the fluid dose by means of the actuating device in relation to the housing. The resetting means mechanically transfers the shift movement of the actuating device into a reverse rotary movement of the counter ring towards its zero position (FIG. 1).

17 Claims, 5 Drawing Sheets

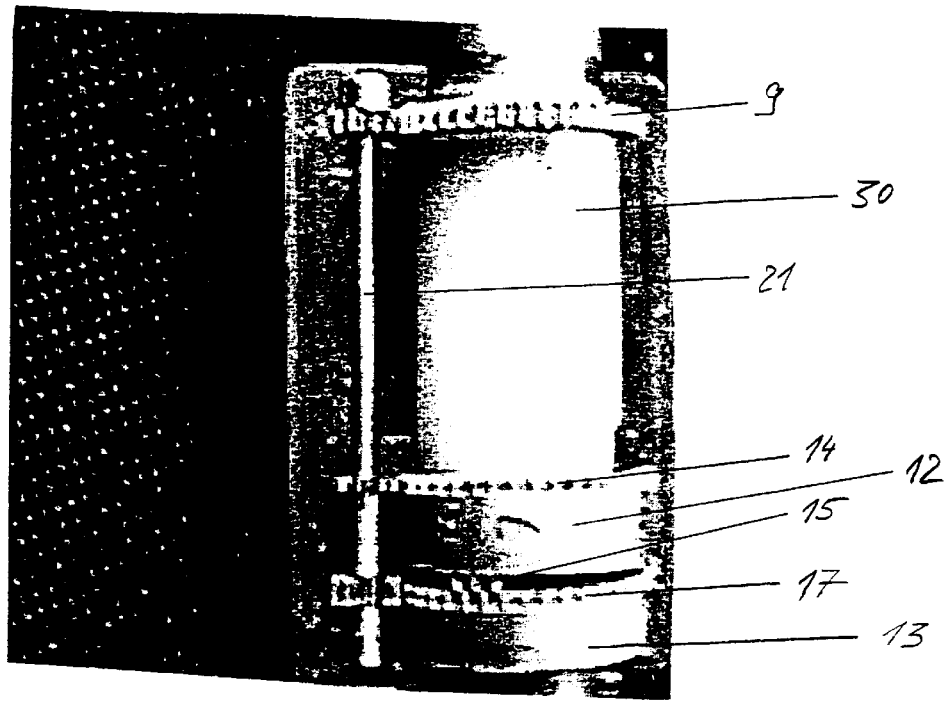
Fig. 2
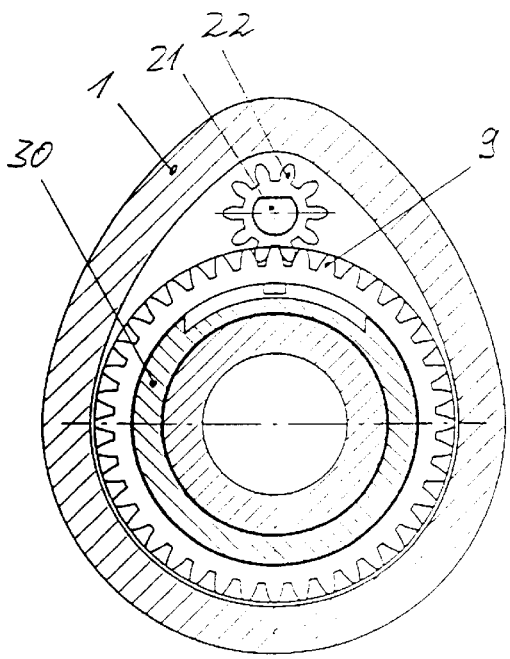
A-A Fig. 3
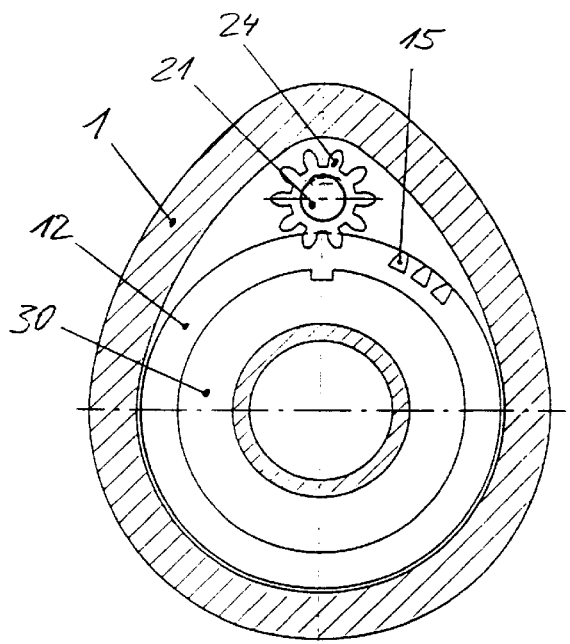
B-B Fig. 4

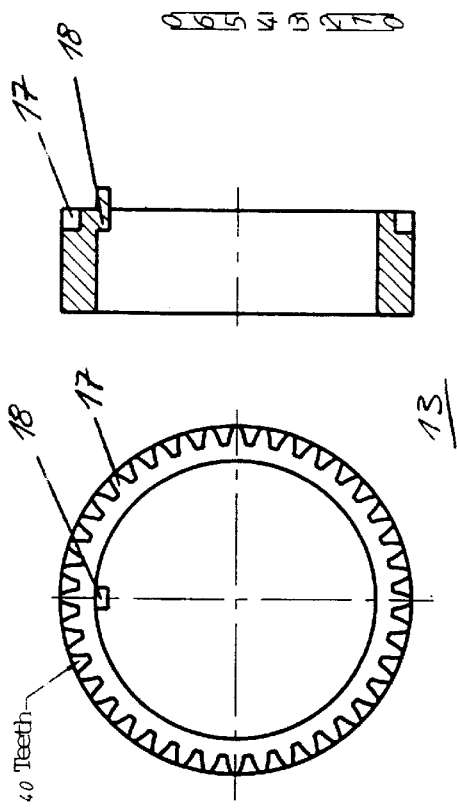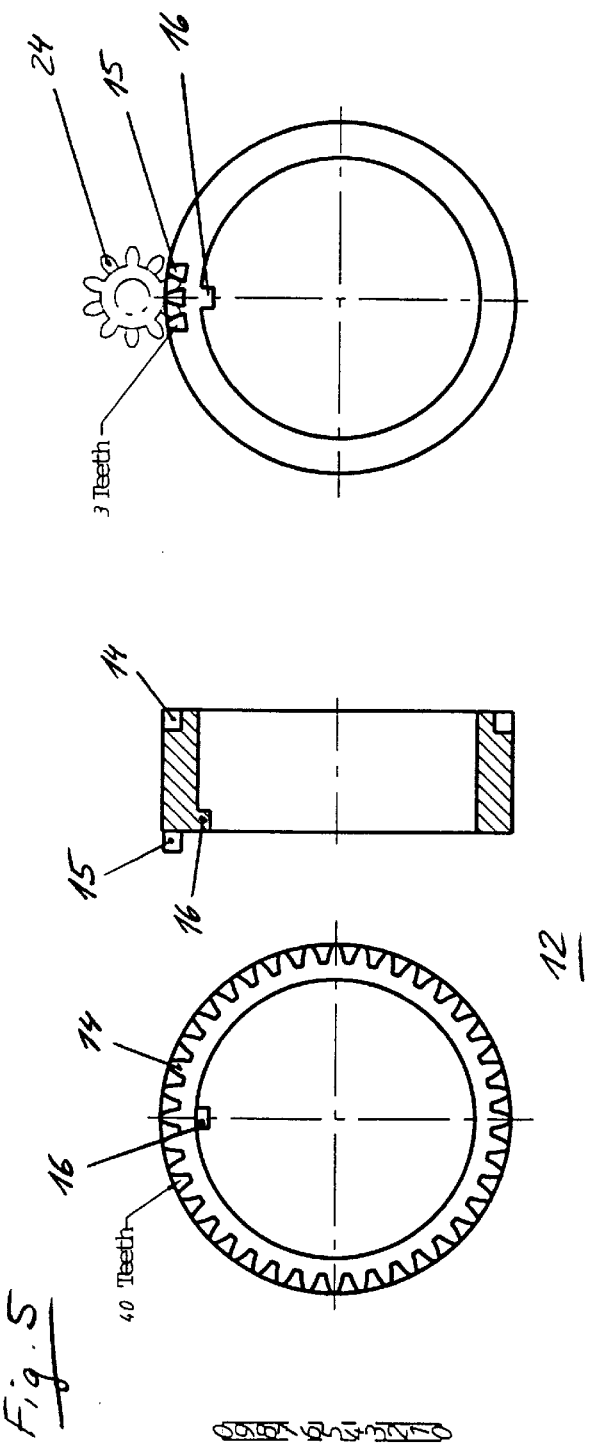

RESETTABLE DISPLAY OF A DEVICE FOR METERED ADMINISTRATION OF A FLUID DRUG

This application claims the priority of German Patent Application No. 197 23 647.2, filed Jun. 5, 1997, which is incorporated herein by reference.

BACKGROUND OF THE INVENTION

1. Field of the Invention

The invention refers to a resettable display of a device for metered administration of a fluid drug, comprising a housing, a fluid container provided in or on the housing and containing the fluid, an actuating device shiftably mounted by a length in or on said housing, which actuating device shifts upon actuation a piston in the fluid container in order to displace from the fluid container a fluid dose adjusted by means of the actuating device, a display provided in or on said housing displaying a measure for the adjusted fluid dose, and a resetting means shifted with the actuating device and thus resetting the display, in which the display comprises a minimum of one counter ring rotated when adjusting the fluid dose from the actuating device in relation to the housing from a zero position, and said resetting means mechanically transfers a shift movement of the actuating device into a reverse rotary movement of the counter ring towards its zero position.

2. Description of the Related Art

A device for the administration of a metered fluid drug is, for instance, known from EP 0 581 925 B1. It is an injection device having the shape of a so-called pen by which a patient can inject himself personally doses of a fluid drug at any time, in particular insulin, to be selected by the patient. The injection equipment comprises an LCD display for display of the fluid drug dose preset by the patient for the next injection. During injection, the display is automatically reset to zero, therefore always displaying the preset fluid dose to be administered for the next injection.

An injection device comprising a mechanical display is known from EP 0 554 996 B1. The preset fluid dose is displayed by two counter rings, a units counter ring and a tens counter ring, provided with suitable scales in order to display the dose preset by the patient in a display window in the housing of the injection device. The display, however, must be reset by the patient after each injection by manually reversing the rotation of the metering and actuating push-button by which the injected fluid dose has been previously preset.

SUMMARY OF THE INVENTION

It is the object of the invention to provide a simple, low-priced, resettable display for a device for metered administration of a fluid drug, which is reset automatically when actuating the device in the course of fluid administration, to a preset position, preferably zero.

This object is achieved by a resettable display of a device for metered administration of a fluid drug, comprising a housing, a fluid container provided in or on the housing and containing the fluid, an actuating device shiftably mounted by a length in or on said housing, which actuating device shifts upon actuation a piston in the fluid container in order to displace from the fluid container a fluid dose adjusted by means of the actuating device, a display provided in or on said housing displaying a measure for the adjusted fluid dose, and a resetting means shifted with the actuating device and thus resetting the display, in which the display comprises a minimum of one counter ring rotated when adjusting the fluid dose by means of the actuating device in relation to the housing from a zero position, and said resetting means mechanically transfers a shift movement of the actuating device into a reverse rotary movement of the counter ring towards its zero position. The use of a counter ring and its mechanical resetting by the resetting means constitutes a rather simple, robust solution for resetting the display.

The device for metered administration of a fluid drug is preferably a portable injection device, in particular a so-called pen. However, the invention may also be advantageously used for stationary dosing devices and devices for administration both by injection and infusion. It is applicable to manually operated devices and also to devices operated by driven pumps. Also it may be beneficial when using pipettes.

Compulsory reverse rotation of the counter ring is preferably effected continuously, i.e. only at the end of the shifting movement of the actuating device. When mechanical transferral of the shifting movement of the actuating device is effected simultaneously with the shifting movement effecting the administration of a fluid, i.e. only at reverse shift of the actuating device, only partial administration of the preset fluid dose can be displayed by partial reverse rotation of the counter ring. If this is unimportant in application, however, shift of the actuating device may be effected during reverse shift after completion of fluid administration.

The shifting movement of the actuating device is preferably transferred by a coulisse or like a coulisse into rotation of the counter ring. The coulisse is formed by a guide track and an engaging means compulsorily guided along the guide track during the shift of the actuating device. The coulisse is preferably designed as a pure slideway, but may also be effected in principle by a rolling movement of the engaging means.

Preferably, the engaging means is firmly connected to the counter ring and the guide track is formed on the resetting means. The guide track may, however, also be formed on the counter ring, preferably on one of the internal circumferential areas of the counter ring, thus allowing in this case firm connection of the engaging means with the resetting means or being formed by the same and being shifted together with the actuating device.

In a preferred embodiment, in which the guide track is formed on said resetting means, the resetting means is of a sleeve-type shape. In the following, it is therefore designated a resetting sleeve. The guide track projects over the surface area of the resetting sleeve.

The rotating axis of the counter ring is preferably formed by its center axis, with the counter ring center axis coinciding with the longitudinal center axis of the actuating device, extending in the direction of shift movement. The counter ring encloses the actuating device coaxially. When reversing the rotation of the counter ring, the guide track is pushed into the annular space between the actuating device and the counter ring. In this design, the engaging means projects radially into the interior, preferably in the shape of a simple cam, from the internal circumference of the counter ring. In principle, the longitudinal center axis of the counter ring and therefore its rotary axis may, however, also be arranged vertically to the shifting direction of the actuating device. A cam projecting, for instance, from one of the faces of the counter ring could be compulsorily guided in a guide track formed as a curved segment with reference to the shifting direction of said actuating device, thus initiating reverse rotation of the counter ring.

The display preferably comprises a minimum of two counter rings, one of which displaying the preset basic dose units and the other displaying the number of complete revolutions of the units counter ring. One complete rotation of the units counter ring preferably corresponds to the setting of ten basic dose units, with one scale division on the tens counter ring corresponding to ten of the said basic dose units each. A display based on a system of tens is particularly user-friendly.

Driving a minimum of one and/or a minimum of two counter rings is preferably effected in the same way as in a mileage counter via a shaft extending parallel to the central longitudinal axis of the counter ring and/or counter rings. This results in a particularly simple and robust drive system which can be used as such without the resetting mechanism and/or the counter rings according to the invention. When used in common injection pens, for instance, the display driven by the principle of a mileage counter offers the advantage that it may be used in this application by incurring very low costs for adaptation.

The units counter ring is rotatable and longitudinally shiftable in relation to the actuating device. It may also be connected to the actuating device non-rotatably but able to be longitudinally shiftable in relation to the actuating device.

BRIEF DESCRIPTION OF THE DRAWINGS

A preferred embodiment of the invention will be described hereafter by drawings, where:

FIG. 2 is a sample for demonstration of the operation of a resettable display of FIG. 1, FIG. 3 is a section on line A—A of FIG. 1, FIG. 4 is a section on line B—B of FIG. 1, FIG. 5 is the first counter ring of the injection device of FIG. 1, FIG. 6 is the second counter ring of the injection device of FIG. 1.

DESCRIPTION OF THE PREFERRED EMBODIMENTS

Figure 1:
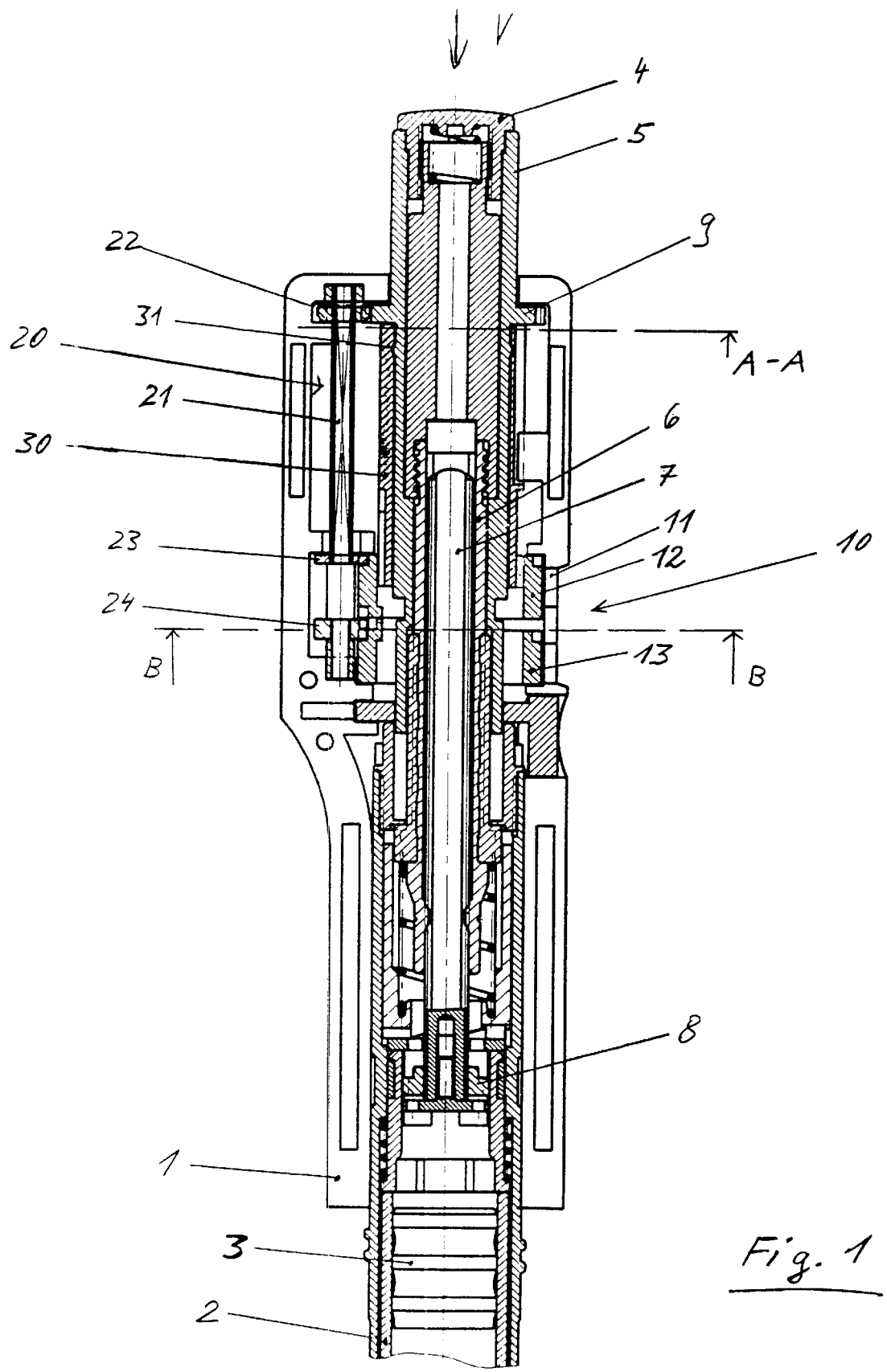
FIG. 1 is a longitudinal section of a portable injection device.

FIG. 1 is a longitudinal section of an injection device having the shape of a so-called pen, comprising a resettable display 10. In addition, the injection device is designed as the device described in WO 93/16740. Therefore the description of the injection device will also cite this reference as a supplement.

The injection device comprises a housing 1 in which a container 2 is accommodated. The container 2 comprises a fluid drug for injection, such as insulin. The container 2 comprises a piston shiftable in the direction of the container outlet. The piston 3 seals the container 2 on one side. When shifting the piston 3 in the direction of the container outlet, injection fluid is displaced from the container.

An actuating device for the piston 3 comprises a metering and actuating push-button including a head section 4 rigidly attached to a sleeve 5. In addition, it comprises a drive sleeve 6 non-rotatably connected to a sleeve 5 and an actuating rod 7 shiftable within the drive sleeve 6 in longitudinal direction of said sleeve 6. The actuating push-button 4, 5 is rotatably supported around the longitudinal axis of the sleeve 6, together with the drive sleeve 6 in said housing 1 in relation to the actuating rod 7. In addition, the actuating rod 7 is shiftably guided and secured against rotation in its front section, facing the piston 3, in a guide means 8 firmly connected to the housing.

A longitudinal shift of the actuating rod 7 is effected in the conventional way, such as described in WO 93/16740, by rotating the actuating push-button 4, 5 and therefore the drive sleeve 6. For this purpose, the drive sleeve 6 with an internal thread and the actuating rod 7 with a suitable external thread engage, thus transferring the rotary movement of the actuating push-button 4, 5 and the sleeve 6 into a shifting movement of the actuating rod 7 in the direction of the piston 3. During rotation, the distance between the piston 3 and the front end of the actuating rod 7 is set. The rotary position of the actuating push-button 4, 5 and therefore of the drive sleeve 6 in relation to the actuating rod 7 is adjustable in discrete steps. Each of these discrete rotary steps corresponds to a basic dose unit of the injection fluid. The actuating device 4 to 7 is in its rear position in the condition shown in FIG. 1. In this position, the drug is metered by rotating the actuating push-button 4, 5 together with the drive sleeve 6 around its central longitudinal axis. After dosage, the actuating device 4 to 7 is shifted along the central longitudinal axis of the drive sleeve 6 in the direction of the arrow V to a stop, formed by the guide means 8, by pressing the actuating push-button 4, 5.

A display 10 operating identical to a mileage counter, comprises two counter rings 12 and 13, rotated around their longitudinal axis, when setting the fluid dose to be administered, by a display-drive mechanism 20. In the following, reference is also made to FIGS. 2 to 4 for explanation of the drive mechanism of the two counter rings 12 and 13.

On its external circumference, the sleeve 5 is provided with an all-round toothed ring 9 by which the display-drive mechanism 20 is driven. The drive mechanism 20 essentially comprises a shaft 21 supported to rotate parallelly to the central longitudinal axis of the drive sleeve 6 within the housing 1 of the injection device. On the shaft 21 are supported non-rotatably in relation to the shaft a first toothed gear 22 engaging in the toothed ring 9 and a second toothed gear 23. A third gear 24 is rotatably supported on the shaft 21. When rotating the actuating push-button 4, 5 and the sleeve 6, the first gear 22 is driven by the toothed ring 9 and consequently compulsorily also the second gear 23 by the shaft 21. The second gear 23 in turn drives the first counter ring 12. The first counter ring 12 is designed as a unit counter ring, i.e. the scale division of its external circumference shows the basic dose units. In order to be driven, the first counter ring 12 is provided with an all-round toothed ring on its sleeve area opposite the second gear 23. In an individual presentation of the first counter ring 12 in FIG. 5, this toothed ring is referred to as 14. From the face of the end of the counter ring 12 facing away from the toothed ring 14 several teeth are projecting in longitudinal direction of the counter ring 12 approximately over the angular area between two subsequent scale divisions of the counter ring 12. In the embodiment, these are three teeth arranged side by side, thus forming a partial toothed ring 15. The partial toothed ring 15 could also be formed on the sleeve face of the counter ring 12 in order to allow the two counter rings 12 and 13 to be brought closer together. At its end facing the partial toothed ring 15, the second counter ring 13 too comprises a toothed ring extending over its complete external circumference. Details of the second counter ring 13 are presented in FIG. 6. In this figure, the toothed ring of the second counter ring 12 is referred to as 17. Preferred dimensions, gear and/or toothed ring designs for an injection pen are shown in FIG. 5 and 6.

When the shaft 21 is driven whilst the sleeve 5 is rotated, the first counter ring 12 is driven by rotation through a pair of teeth 23/14. Beneath the sight window 11, basic dose units, as shown in embodiments 0 to 9, are being displayed, by which the actuating push-button 4, 5 and the sleeve 6 have been rotated from zero position. The tens counter ring 13 is rotated forward by one scale division for each complete rotation of the first counter ring 12. When the partial toothed ring 15 of the first counter ring 12 has been rotated to the level of the third gear 24, the third gear 24 acts as a tight coupling between the two counter rings 12 and 13 when continuing to rotate the first counter ring 12. Rotation of the third gear 24 and therefore the second counter ring 13 is continued depending on the size of the partial toothed ring 15. As soon as the partial toothed ring 15 has been rotated past the third gear 24, there is no longer a drive connection between the first counter ring 12 and the second counter ring 13.

Once the desired dose has been adjusted and is displayed by the two counter rings 12 and 13 beneath the sight window 11, the actuating device 4 to 7 is advanced in the direction of the arrow V. When advancing, the gear pair 9/22 is disengaged and the two counter rings 12 and 13 may be rotated without limitation. When advancing the actuating device 4 to 7, the counter rings 12 and 13 are reversed in the direction of their zero position. Transferral of this advance into a reverse rotary movement of the counter ring 5 is effected by a restraining guide, i.e. a resetting sleeve 30. The resetting sleeve 30 is secured against rotation and longitudinal displacement to the sleeve 5. It is arranged in close proximity to the external circumference of the sleeve 5 in order to save space. On advance of the actuating device 4 to 7, it is displaced below the first counter ring 12 up to the level of the second counter ring 13.

As previously shown in FIG. I but more clearly in FIG. 5 and 6, both the first counter ring 12 and the second counter ring 13 each comprise a radial interior projection 16 and 18 respectively on their internal circumference. The two projections 16 and 18 are each formed on the two ends of the two counter rings 12 and 13 facing each other. These two projections and/or cams 16 and 18 are co-acting with the resetting sleeve 30 as a coulisse for resetting and zeroing the two counter rings 12 and 13. During advance of the resetting sleeve 30 in the direction of the piston 3, the two projections 16 and 18 are subject to restrained guidance by sliding along a guide track of the sleeve surface of the resetting sleeve 30 until their desired position, zero position in the embodiment, is reached. In the embodiment, restrained guidance is formed by a pure slideway.

Figure 7:
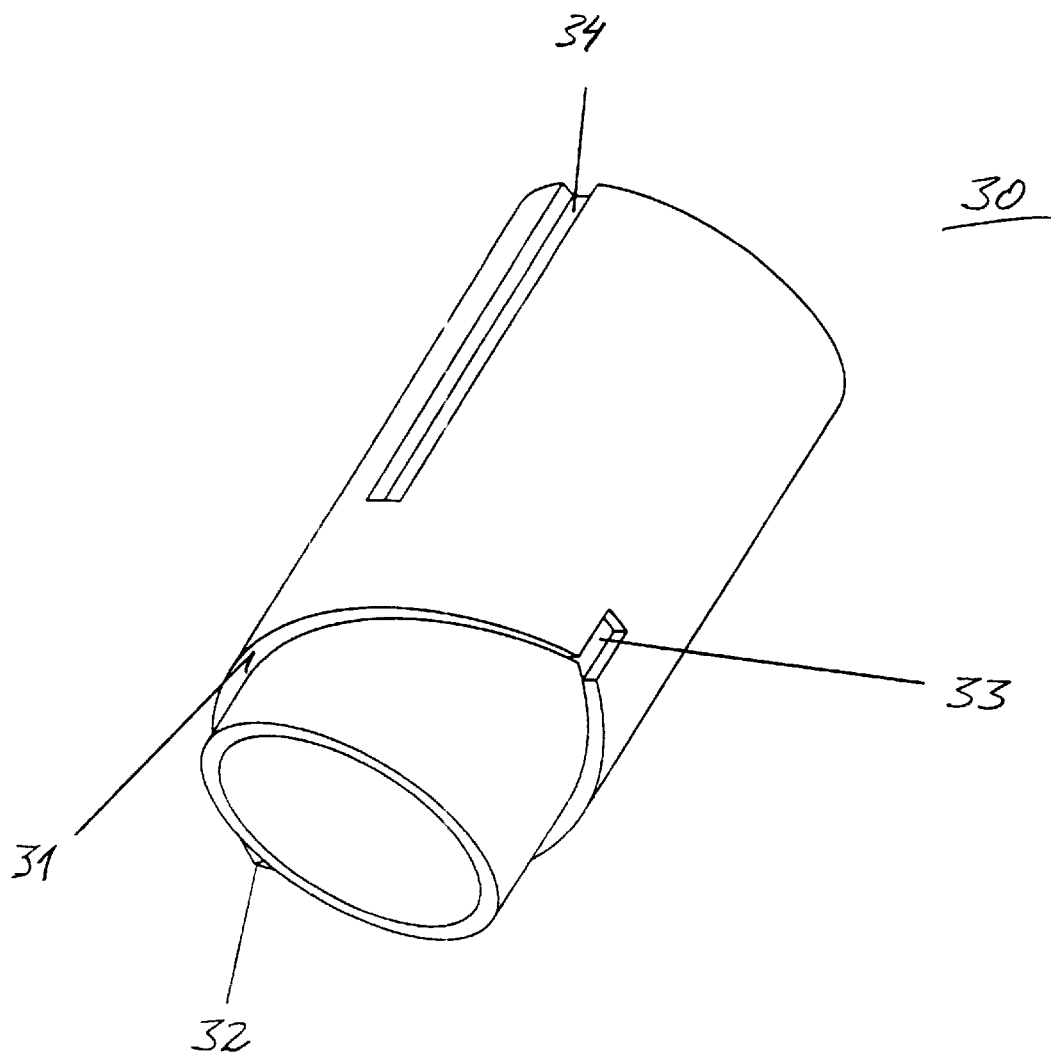
FIG. 7 is the resetting sleeve of the injection device of FIG. I and FIG. 8 is a longitudinal section and two front views of the resetting sleeve of FIG. 7.
Figure 8:
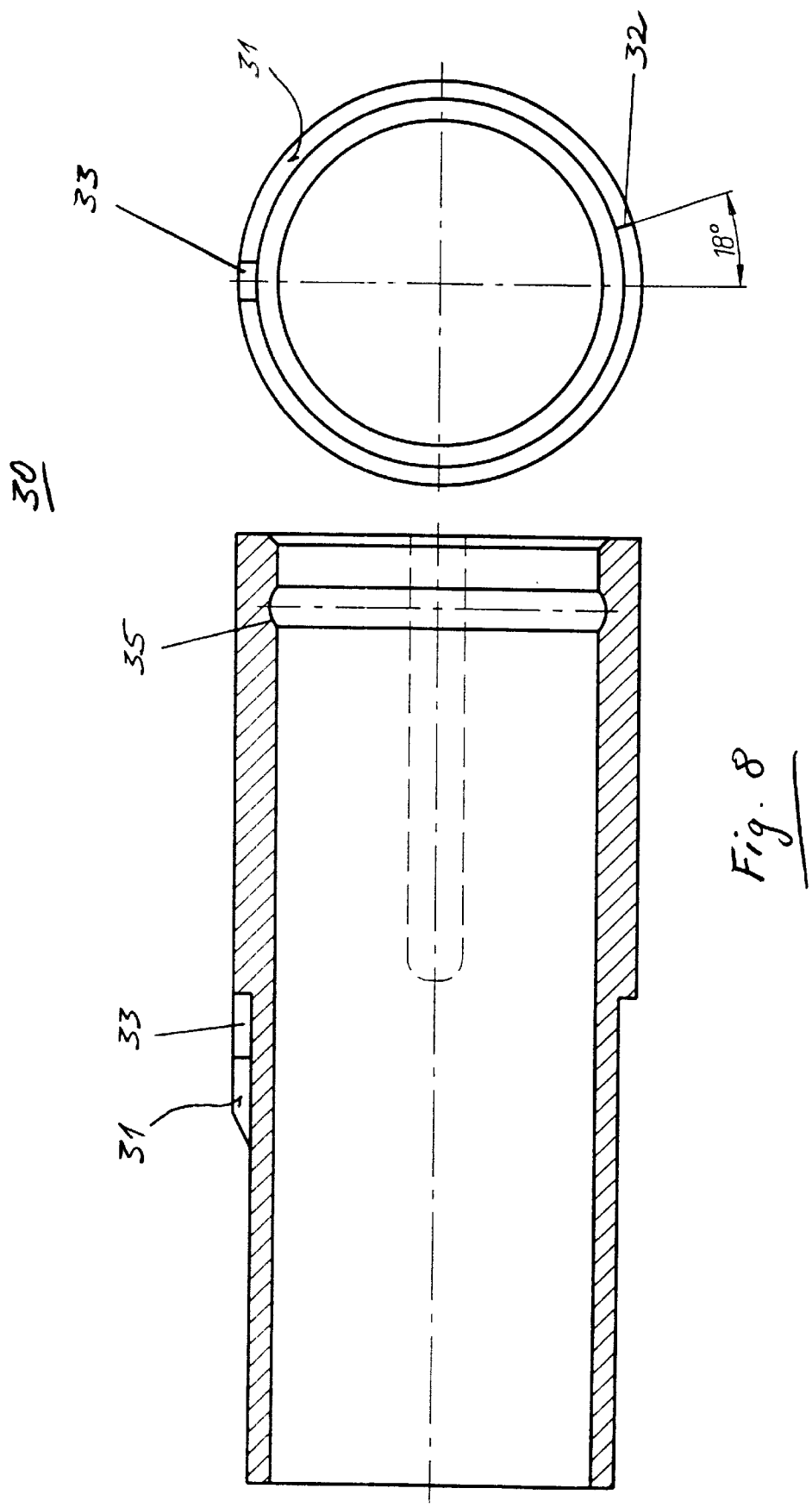

In FIG. 7, the resetting sleeve 30 is shown as an exploded view. FIG. 8 shows a longitudinal section and two front views of the resetting sleeve 30 including preferred dimensions. At its end facing the counter rings 12 and 13, the resetting sleeve 30 comprises a guide track 31 on its external circumference over which the projections 16 and 18 are restrained in sliding when pushing over the resetting sleeve 30, thus transferring the longitudinal movement of the actuating device 4 to 7 and therefore the resetting sleeve 30 during injection into a rotary movement of the two counter rings 12 and 13 in the direction of their respective zero position. The guide track 31 projects approximately radially from the external circumferential area of the resetting sleeve 30. The face of the guide track 31 facing the projections 16 and 17 forms a sliding face for the two projections. The guide track 31 slides, therefore, commencing from a front tip 32 facing the two projections 16 and 18 downwards either side of the tip 32 from the projections 16 and 18, in a V-shape, when shown in a developed view of the guide track 31, ending in a groove 33 extending in longitudinal direction of the resetting sleeve 30. The tip 32 is not exactly diagonally opposite the groove 33 but is offset in relation to center position by half the angle between two basic dose units on the first counter ring 12. The gradient of the guide track 31 with reference to the longitudinal axis of the resetting sleeve 30 is constant from the tip 32 to the groove 33. The gradients on the right-hand and left-hand side of the tip 32 are different due to the offset arrangement of the tip 32 in relation to the groove 33. In zero position of the two counter rings 12 and 13, these two projections 16 and 18 are located in line in the groove 33.

In order to obtain a maximum extension and therefore the least friction for the guide track 31, seen in longitudinal direction of the actuating device 4 to 7, the advance of the actuating device 4 to 7 is used as far as possible for the guide track 31. For this purpose, the front tip 32 of the guide track 31 projects in closest proximity to the two projections 16 and 18. The projections 16 and 18 on the other hand are located in closest proximity to each other in longitudinal direction of the two counter rings 12 and 13. In order to bridge the distance between the counter rings 12 and 13, specified by the height of the partial toothed ring 15 in the embodiment, the projection 18 of the counter ring 13, which is further away from the resetting sleeve 30, is extended beyond the face of the counter ring 13 towards the counter ring 12 by a corresponding piece, as shown in FIG. 6.

The resetting sleeve 30 is initially attached by being slid on the sleeve 5. As a security against rotation, a longitudinal groove 34 provided in one end of the resetting sleeves 30 facing away from the counter rings 12 and 13, into which a suitable longitudinal rib projecting into the interior of the housing engages, along which the resetting sleeve 30 is sliding and is secured against rotation. Axial attachment is provided by means of a cambered ring surrounding the actuating sleeve 5 over which the resetting sleeve 30 is pushed, resting in a ring 35 (FIG. 8) accordingly recessed in the internal circumference of the resetting sleeve 5, therefore allowing the resetting sleeve 30 to be secured on the sleeve 5 against shift. The resetting sleeve 30 is easy to manufacture, whereby a material is used which provides an excellent sliding match in connection with the projections 16 and 18.

We claim:

1. A resettable display of a device for metered administration of a fluid, comprising:

a) a housing, b) a fluid container provided in or on the housing and containing the fluid, the fluid container having a piston, c) an actuating device shiftably mounted by a length in or on said housing, wherein upon actuation the actuating device shifts the piston in the fluid container in order to displace from the fluid container a fluid dose adjusted by means of the actuating device, d) a display provided in or on said housing displaying a measure for the adjusted fluid dose, and e) a resetting means shifted with the actuating device and thus resetting the display, in which the resetting means includes a guide track and in which the display comprises a first counter ring rotated when adjusting the fluid dose by means of the actuating device in relation to the housing from a zero position, said counter ring carrying a projection for engaging said guide track, whereby said resetting means mechanically transfers a longitudinal movement of the actuating device into a reverse rotary movement of the first counter ring towards its zero position.

2. A resettable display according to claim 1, in which the guide track runs around a central longitudinal line of the first counter ring.

3. A resettable display according to claim 1, in which the engaging projection is formed by a radial internal projection from an internal circumferential surface of the first counter ring.

4. A resettable display according to claim 1, in which the first counter ring is driven by adjusting the fluid dose to be administered in an identical manner to a mileage counter, in which a rotary movement of a metering and actuating push-button of the actuating device is transferred to a shaft rotatably supported in or on the housing and the rotary movement of the shaft is transferred to the first counter ring via a toothed gear non-rotatably mounted on the shaft.

5. A resettable display according to claim 4, in which the shaft is arranged parallel to the rotary axis of the metering and actuating push-button of the actuating device.

6. A resettable display of a device for metered administration of a fluid, comprising:
  a) a housing,
  b) a fluid container provided in or on the housing and containing the fluid, the fluid container having a piston,
  c) an actuating device shiftably mounted by a length in or on said housing, wherein upon actuation the actuating device shifts the piston in the fluid container in order to displace from the fluid container a fluid dose adjusted by means of the actuating device,
  d) a display provided in or on said housing displaying a measure for the adjusted fluid dose, and
  e) a resetting means shifted with the actuating device and thus resetting the display, in which the resetting means includes a guide track and in which the display comprises a first counter ring rotated when adjusting the fluid dose by means of the actuating device in relation to the housing from a zero position, said counter ring carrying a projection for engaging said guide track, whereby said resetting means mechanically transfers a longitudinal movement of the actuating device into a reverse rotary movement of the first counter ring towards its zero position, wherein the resetting means contains a front track end and a track base, and wherein the guide track extends in two directions from the front track end towards the track base and the engaging means is guided in the direction toward the track base when shifting the resetting means.

7. A resettable display according to claim 6, in which the guide track extending from the front track end terminates in a longitudinal groove at the track base.

8. A resettable display according to claim 6, in which the front track end is offset from a diagonally opposite central position in relation to the track base.

9. A resettable display of a device for metered administration of a fluid, comprising:
  a) a housing,
  b) a fluid container provided in or on the housing and containing the fluid, the fluid container having a piston,
  c) an actuating device shiftably mounted by a length in or on said housing, wherein upon actuation the actuating device shifts the piston in the fluid container in order to displace from the fluid container a fluid dose adjusted by means of the actuating device,
  d) a display provided in or on said housing displaying a measure for the adjusted fluid dose, and
  e) a resetting means shifted with the actuating device and thus resetting the display, in which the resetting means includes a guide track and in which the display comprises a first counter ring rotated when adjusting the fluid dose by means of the actuating device in relation to the housing from a zero position, said counter ring carrying a projection for engaging said guide track, whereby said resetting means mechanically transfers a longitudinal movement of the actuating device into a reverse rotary movement of the first counter ring towards its zero position, in which the resetting means contains a sleeve face and is sleeve-shaped and the guide track is formed on the sleeve face of the resetting means.

10. A resettable display of a device for metered administration of a fluid, comprising:
  a) a housing,
  b) a fluid container provided in or on the housing and containing the fluid, the fluid container having a piston,
  c) an actuating device shiftably mounted by a length in or on said housing, wherein upon actuation the actuating device shifts the piston in the fluid container in order to displace from the fluid container a fluid dose adjusted by means of the actuating device,
  d) a display provided in or on said housing displaying a measure for the adjusted fluid dose, and
  e) a resetting means shifted with the actuating device and thus resetting the display, in which the resetting means includes a guide track and in which the display comprises a first counter ring rotated when adjusting the fluid dose by means of the actuating device in relation to the housing from a zero position, said counter ring carrying a projection for engaging said guide track, whereby said resetting means mechanically transfers a longitudinal movement of the actuating device into a reverse rotary movement of the first counter ring towards its zero position, in which a second counter ring is arranged flush with the first counter ring, and wherein the first counter ring displays basic dose units and the second counter ring displays the number of revolutions of the first counter ring.

11. A resettable display of a device for metered administration of a fluid, comprising:
  a) a housing,
  b) a fluid container provided in or on the housing and containing the fluid, the fluid container having a piston,
  c) an actuating device shiftably mounted by a length in or on said housing, wherein upon actuation the actuating device shifts the piston in the fluid container in order to displace from the fluid container a fluid dose adjusted by means of the actuating device,
  d) a display provided in or on said housing displaying a measure for the adjusted fluid dose, and
  e) a resetting means shifted with the actuating device and thus resetting the display, in which the resetting means includes a guide track and in which the display comprises a first counter ring rotated when adjusting the fluid dose by means of the actuating device in relation to the housing from a zero position, said counter ring carrying a projection for engaging said guide track, whereby said resetting means mechanically transfers a longitudinal movement of the actuating device into a reverse rotary movement of the first counter ring towards its zero position, in which the first counter ring is driven by adjusting the fluid dose to be administered in an identical manner to a mileage counter, in which a rotary movement of a metering and actuating push-button of the actuating device is transferred to a shaft rotatably supported in or on the housing and the rotary movement of the shaft is transferred to the first counter ring via a toothed gear non-rotatably mounted on the shaft, and in which a second toothed gear is rotatably supported by the shaft, the second toothed gear being in constant engagement with a toothed ring formed on a second counter ring and in turn being driven by a partial toothed ring of the first counter ring when the first counter ring completes a full rotation and that the angular area spanned by the partial toothed ring corresponds to the angular area of a scale division of the second counter ring.

12. A device for metered administration of a fluid, comprising:

a) a housing;

b) an actuating device movably coupled to the housing, wherein the actuating device rotates for selecting a dose of the fluid and longitudinally shifts for administering the selected dose;

c) a display associated with the housing for displaying the selected dose, the display having at least one counter ring rotated from a zero position when selecting the fluid dose, said counter ring carrying a projection; and d) a resetting sleeve movably attached within the housing and carrying a guide track for receiving the projection, wherein during administration of the dose, the interaction of the projection and the guide track of the resetting sleeve transfers the longitudinal movement of the actuating device into rotary movement of the at least one counter ring to reset the at least one counter ring to the zero position.

13. The device of claim 12, wherein the actuating device comprises a metering and actuating push-button having a head section and a first sleeve, a drive sleeve non-rotatably connected to the first sleeve, and an actuating rod movably mounted within the drive sleeve.

14. The device of claim 12, wherein the resetting sleeve contains a tip at a front end and a groove at a back end, and wherein the guide track extends in two directions from the tip to the groove and the at least one projection is guided along the guide track toward the groove when the actuating rod is longitudinally shifted.

15. The device of claim 12, wherein the at least one projection is formed by a radial internal projection from an internal circumferential surface of the counter ring.

16. The device of claim 12, wherein the counter ring comprises a first counter ring and a second counter ring arranged flush with the first counter ring, and wherein the first counter ring displays basic dose units and the second counter ring displays the number of revolutions of the first counter ring.

17. A device for metered administration of a fluid comprising:

a) a housing;

b) an actuator movably coupled to the housing, wherein a longitudinal movement of the actuator causes a fluid dose to be administered;

c) a display associated with the housing, wherein rotation of the actuator causes the display to display the fluid dose to be administered said display comprising a counter ring carrying a projection; and d) a resetting sleeve operably coupled to the actuating device, said resetting sleeve carrying a guide track for receiving the projection, wherein, upon administering the fluid dose, the interaction of the projection and the guide track of the resetting sleeve automatically resets the display.

* * * * *